United States Patent [19]

Abe et al.

[11] 4,202,348
[45] May 13, 1980

[54] KOROTKOV SOUND SENSOR

[75] Inventors: Akira Abe, Takatsuki; Shoji Kimura, Kameoka; Yuzo Kuwabara, Kyoto, all of Japan

[73] Assignee: Omron Tateisi Electronics Co., Kyoto, Japan

[21] Appl. No.: 826,245

[22] Filed: Aug. 19, 1977

[30] Foreign Application Priority Data

Sep. 10, 1976 [JP] Japan ............... 51/122034[U]

[51] Int. Cl.² .............................................. A61B 5/02
[52] U.S. Cl. .................................. 128/680; 179/1 ST
[58] Field of Search ............ 128/2.05 C, 2 K, 2.05 S, 128/680, 715, 773; 181/131, 132, 137, 157; 179/115 R, 1 ST

[56] References Cited

U.S. PATENT DOCUMENTS

| D. 185,178 | 5/1959 | Spears | 181/131 |
|---|---|---|---|
| 910,854 | 1/1909 | Pilling | 128/2 K |
| 2,271,467 | 1/1942 | Smithline | 181/131 |
| 2,699,465 | 1/1955 | Hamilton | 128/2.06 R |
| 3,148,677 | 9/1964 | Smith | 128/2.05 S |
| 3,416,516 | 12/1968 | Cohen et al. | 179/107 R X |
| 3,633,703 | 1/1972 | Littman | 128/2.05 S |
| 4,141,350 | 2/1979 | Shinoda | 128/2.05 C |

*Primary Examiner*—Robert W. Michell
*Assistant Examiner*—Francis J. Jaworski
*Attorney, Agent, or Firm*—Stevens, Davis, Miller & Mosher

[57] ABSTRACT

A Korotkov sound sensor having a microphone in a housing body which is nearly rectangular in shape, made of elastic material and having a hollow therein. A flexible thin film to be placed adjacent an artery of an individual is adhered to the periphery of the hollow to form an air space. The housing body hardly transmits external noises to the microphone, and Korotkov sounds from an artery of the individual are transmitted to the microphone through the thin film and the air space. Highly sensitive and accurate measurement of blood pressure is easily achieved by this system.

4 Claims, 5 Drawing Figures

KOROTKOV SOUND SENSOR

BACKGROUND OF THE INVENTION

This invention relates to a Korotkov sound sensor for use with an electronic sphygmomanometer for electrically discriminating Korotkov sounds.

The typical recently developed electronic sphygmomanometer has a microphone incorporated in a cuff which occludes blood flow. The blood pressure of an individual is measured when the cuff is wrapped around the arm of an individual to position the microphone over or adjacent an artery below the blood-occluding portion of a cuff.

Since the microphone for such a sphygmomanometer is disc-shaped and is positioned over the artery, positioning the microphone on the arm of an individual affects the accuracy of detecting Korotkov sounds and is a major reason for introduction of errors and difficulty in the measurement of blood pressure by inexpert persons.

Various types of Korotkov sound sensors have been developed to measure blood pressure with high sensitivity and high accuracy independent of the skill of the individual. For example, an inflatable cuff for detecting Korotkov sounds is jointly used with an inflatable cuff for occluding blood flow and a small-sized microphone is applied to the end of the pressure guide tube which is connected between the cuffs. The sound pick up area in that structure is so wide, since the microphone receives Korotkov sounds transmitted through the air in the inflatable cuff for detecting Korotkov sounds, that positioning of the microphone is not a problem. However, such structure shows a tendency to generate or pick up various noises, especially when the individual touches the cuffs or the pressure guide tube connected between the cuffs. As a result, easy and accurate measurement of blood pressure is not achieved.

SUMMARY OF THE INVENTION

The purpose of the present invention is to obviate the above described problems in the prior art. The present invention provides a Korotkov sound sensor comprising a housing body, a thin film, and a microphone, the housing body being made of elastic material having a hollow therein, the thin film being adhered to the periphery of the hollow to form an air space or "room" between the thin film and the housing body, the microphone being installed in the housing body, so that the Korotkov sounds are thereby transmitted to the microphone through the thin film and the air space, being detected by the microphone when the thin film is placed over an artery of an individual.

In the preferred embodiment, the housing body is shaped like a rectangular board and is curved to make it fit around the arm of an individual, and the hollow made in a main surface of the housing body is long and narrow so that the air room or Korotkov sound pick up area is enlarged in a direction to cross an artery in the arm of the individual. The sensor hardly generates or picks up external noise since the Korotkov sound pick up area is formed by the elastic housing body and flexible thin film, the former hardly transmitting noises to the microphone and only the latter permitting sounds to pass, including Korotkov sounds from the arm of the individual to the microphone.

By this system, easy and accurate measurement of blood pressure is achieved by even inexpert persons.

DESCRIPTION OF THE PREFERRED EMBODIMENTS

Figure 1:
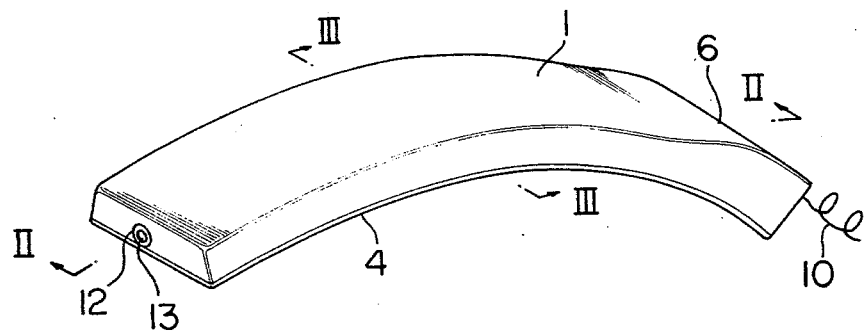
FIG. 1 is a perspective view of the sensor of the present invention.
Figure 2:
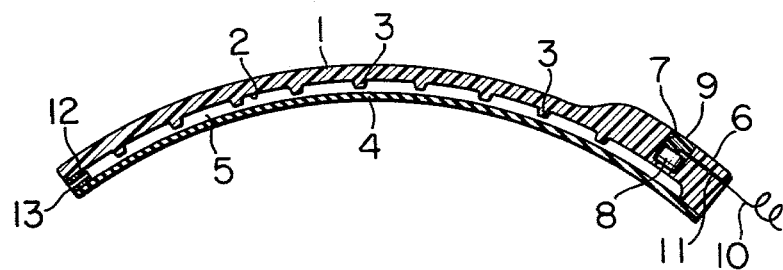
FIG. 2 is a sectional view taken along line II—II in FIG. 1.

In the drawings numeral 1 shows the housing body made of elastic material such as rubber or plastic, being in nearly rectangular board shape, having an approximate length of 10 cm, approximate width of 2.5 cm, approximate height of 6 mm, and being curved for fitting around the arm. A hollow 2 on air chamber, having an approximate depth of 3 mm, is formed on the concave side of the housing body only the peripheral portions of which are retained. A number of projections 3 are located in a line along the length of the interior of the hollow 2. Sound pick up thin film 4, having an approximate thickness of 0.5–1 mm, made of flexible and expansible material such as rubber or plastic is adhered to the periphery of the concave surface of the housing body 1 to form the air chamber or space 5 between the sound pick up thin film 4 and the surface of hollow 2. A thick portion 6, having approximate height of 1 cm, is formed at the end of the convex portion of the housing body 1, being integral with the housing body 1.

A hole 7 passing through the thick portion 6 to the air chamber 5 is formed to hold a microphone therein. A disc-shaped miniaturized condenser microphone 8, which is ordinarily used in audio-equipment, is inserted into the hole 7, with its sound pick up side facing the air space 5, and is fixed in the hole by a stopper 9 made of rubber etc. This system is thus just as if the microphone 8 was molded into the thick portion 6 of the housing body 1. Conductive leads 10 of the microphone are led to the outside of the housing body through a hole 11 formed in the thick portion of the housing body. The microphone 8 may be built into another portion of the housing body 1 such as the middle of the housing body 1. A hole 12 passing through the side wall of the housing body 1 is formed at the other end of the housing body 1 to make the air chamber open to the outside, and a tube 13 with proper inside diameter is inserted into the hole so that the sectional area of the path between the air chamber 5 and the outside depends on the inside diameter of the tube 13. The tube 13 is useful to pass pulse sounds transmitted to the air chamber through the thin film to the outside of the housing body and to reduce the pressure in the air room when the sensor is attached to the arm of the individual.

Figure 3:
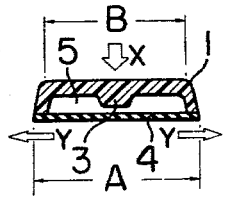
FIG. 3 is a sectional view taken along line III—III in FIG. 1.

In measuring blood pressure by using the thus constructed Korotkov sound sensor, the sensor is attached to the pocket on the interior side of the cuff for occluding blood flow (not shown in the drawings) and the cuff is wrapped around the arm in order to touch, directly or indirectly, the sound pick up thin film 4 to the arm of the individual, then the cuff is inflated to occlude the blood flow. The Korotkov sounds generated during exhausting air from the cuff are transmitted to the air chamber 5 through the film 4 and further transmitted to the microphone 8 by the air in the air chamber 5. The housing body 1 has a reasonable thickness, shape, and rigidity to maintain the air chamber 5 even if high pressure is applied to the sensor during the inflation of the cuff. Namely, the housing body 1 is made of elastic material having reasonable hardness and thickness maintaining the shape of the air chamber 5 while it curves and the shape of the air chamber 5 is changed depending on the size of the arm. The projections 3 operate as spacers maintaining the gap between the inner surface of the hollow 2 and the sound pick up thin film 4 when the sensor is attached to the arm of the individual. As is shown in FIG. 3, the sectional feature of the housing body 1 is an isosceles trapezoid with long base A corresponding to the width of the concave side and short base B corresponding to the width of the convex side. Also, the sectional feature of the air chamber 5 is an isosceles trapezoid. Other sectional shapes of the housing body 1 and the air chamber 5, such as a half circle or triangle may be also used. When pressure is applied to the above-described construction in the direction of the arrow X, the housing body 1 is deformed while it generates force in the direction of the arrow Y tensioning the sound pick up thin film 4 so that no folds, wrinkles or creases occur in the film.

In consideration of the anti-noise characteristics, noises such as pulse sounds from the cuff are hardly transmitted to the air chamber since the air chamber 5 is enclosed by the rather thick wall of housing body 1 except at the sound pick up thin film 4. Further, no noise is generated or collected in the sound transmitting path between the air chamber 5 and the microphone 8 since the microphone 8 is molded into the thick wall of the housing body 1 and directly faces the air chamber 5, so that a very high signal to noise ratio is obtained. The sensitivity and frequency characteristics of the sensor are adjusted by adjustment of the inner diameter of the tube 13 since the sound characteristics of the air chamber 5 depend on the inner diameter of the tube 13 which connects the air chamber 5 with the exterior of the housing body.

Figure 4:
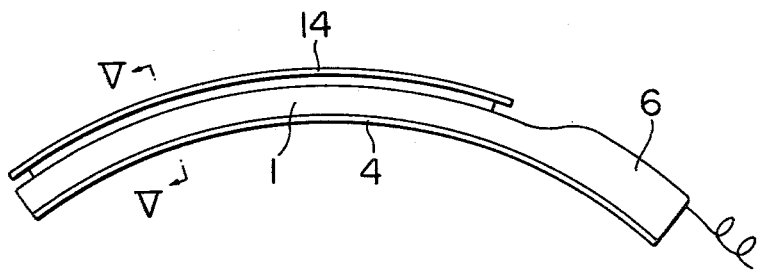
FIG. 4 is an elevational view of the sensor in another embodiment of the present invention.
Figure 5:
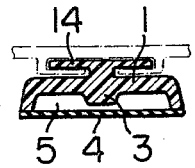
FIG. 5 is a sectional view taken along line V—V in FIG. 4.

FIG. 4 and FIG. 5 show another embodiment of this invention including structure for attaching the sensor to the cuff. A long and narrow attachment piece 14 of T-shaped cross section is attached to the convex exterior side of the housing body 1. A long and narrow acceptor, partically shown in dotted lines in FIG. 5, complementary to the attachment piece 14 is attached to the inside cover of the cuff (not shown). The sensor is thus attached to the cuff, not using the pocket of the cuff as mentioned above, but by inserting the T-shaped attachment piece 14 into the complementary acceptor. In this embodiment, the housing body 1 is deformed to apply tension to the sound pick up film 4 since the attachment piece 14 also operates as a rib when pressure from the cuff is applied to the attachment piece 14.

As shown above, the Korotkov sound sensor for an electronic sphygmomanometer of the present invention enables highly sensitive and high anti-noise characteristics detection of Korotkov sounds independent of the accuracy of the positioning the sensor, providing a system for easy and accurate measurement of blood pressure even by inexpert individuals.

What is claimed is:

1. A Korotkov sound sensor for an electronic syphgmomanometer comprising:
   a curved housing body of elastic material having a hollow therein, said housing body having a length and a width forming a substantially rectangular shape, said hollow having a length and width, said housing body including a top portion, and lengthwise and widthwise sidewalls depending from said top portion, said body including an external microphone support portion which is thicker than the remainder of said body and which has a through hole therein, said lengthwise sidewalls flaring outwardly of said body and causing widthwise expansion of said hollow when external pressure is applied to said top portion;
   an expansible thin film, adapted to be placed adjacent an artery of an individual, attached to the depending sidewalls of the curved housing body and forming a curved air chamber in the hollow between the thin film and the body;
   a plurality of spaced projections formed on said housing body in said hollow along the lengthwise direction of said body for preventing said thin film from contacting the bottom of said hollow, each said projection having a length which is less than the width of said hollow; and,
   a microphone mounted in said through hole in direct communication with said air chamber for detecting Korotkov sounds transmitted through the thin film and the air chamber.

2. The Korotkov sound sensor of claim 1, wherein the housing body includes a small through-hole communicating between the air chamber and the exterior of the body.

3. The Korotkov sound sensor of claim 1, wherein the housing body further comprises attachment means located on the exterior thereof on a center line along the length of said body for attaching said housing body to a cuff and for distributing pressure applied thereto to said sidewalls.

4. The Korotkov sound sensor of claim 1 wherein said projections do not contact said thin film when said sound sensor is not in use.

* * * * *